United States Patent
Chung et al.

(10) Patent No.: US 10,779,841 B2
(45) Date of Patent: Sep. 22, 2020

(54) DRILLING DRIVER FOR PLACING DENTAL IMPLANT

(71) Applicant: GENOSS CO., LTD., Suwon-si, Gyeonggi-do (KR)

(72) Inventors: Sung-Min Chung, Suwon-si (KR); Sung-Geun Lee, Suwon-si (KR); Seung-Woo Suh, Suwon-si (KR)

(73) Assignee: GENOSS CO., LTD., Suwon (KR)

( * ) Notice: Subject to any disclaimer, the term of this patent is extended or adjusted under 35 U.S.C. 154(b) by 305 days.

(21) Appl. No.: 15/756,060

(22) PCT Filed: Jul. 29, 2016

(86) PCT No.: PCT/KR2016/008357
§ 371 (c)(1),
(2) Date: Mar. 19, 2018

(87) PCT Pub. No.: WO2017/039158
PCT Pub. Date: Mar. 9, 2017

(65) Prior Publication Data
US 2018/0235737 A1    Aug. 23, 2018

(30) Foreign Application Priority Data
Aug. 31, 2015    (KR) .................. 10-2015-0122804

(51) Int. Cl.
*A61B 17/16*    (2006.01)
*A61C 3/02*    (2006.01)

(52) U.S. Cl.
CPC ............ *A61B 17/1673* (2013.01); *A61C 3/02* (2013.01)

(58) Field of Classification Search
CPC . A61B 17/16; A61B 17/1613; A61B 17/1615; A61B 17/1617; A61B 17/162;
(Continued)

(56) References Cited

U.S. PATENT DOCUMENTS

| 2,902,763 | A | * | 9/1959 | Heppe | A61C 3/02 433/165 |
| 4,345,899 | A | * | 8/1982 | Vlock | A61C 3/02 408/226 |

(Continued)

FOREIGN PATENT DOCUMENTS

| JP | 2561697 B2 | 12/1996 |
| JP | 2013-500073 A | 1/2013 |

(Continued)

OTHER PUBLICATIONS

International Search Report dated Dec. 1, 2016 in PCT/KR2016/008357, 4pgs.

*Primary Examiner* — Eric S Gibson
(74) *Attorney, Agent, or Firm* — Ichthus International Law PLLC

(57) ABSTRACT

The present disclosure provides a drilling driver for placing a dental implant. The drilling driver includes: a tip part having a first outer diameter and having a cutting edge; a small-diameter part extended from the tip part, and having a second outer diameter smaller than the first outer diameter; and a large-diameter part positioned farther from the tip part than the small-diameter part, and having a third outer diameter larger than the first outer diameter.

6 Claims, 1 Drawing Sheet

(58) Field of Classification Search
CPC ............ A61B 17/1655; A61B 17/1662; A61B 17/1673; A61B 17/1657; A61C 3/02
See application file for complete search history.

(56) References Cited

U.S. PATENT DOCUMENTS

| | | | | |
|---|---|---|---|---|
| 5,664,914 A * | 9/1997 | Taniguchi | ............... | B23B 51/00 408/199 |
| 5,735,690 A * | 4/1998 | Malentacca | ............... | A61C 3/02 433/102 |
| 5,816,807 A * | 10/1998 | Matsutani | ............... | A61C 3/02 433/165 |
| 9,987,727 B2 * | 6/2018 | Wiand | ............... | B24D 3/06 |
| 2001/0004518 A1 * | 6/2001 | Murai | ............... | A61C 5/42 433/102 |
| 2003/0159544 A1 * | 8/2003 | Moser | ............... | B21C 23/147 76/108.6 |
| 2003/0232307 A1 * | 12/2003 | Beppu | ............... | A61C 3/02 433/165 |
| 2006/0105293 A1 * | 5/2006 | Funato | ............... | A61C 3/02 433/165 |
| 2006/0228669 A1 * | 10/2006 | Scianamblo | ............... | A61C 5/42 433/102 |
| 2007/0082318 A1 * | 4/2007 | Breguet | ............... | A61C 5/42 433/102 |
| 2009/0170053 A1 * | 7/2009 | Ikemi | ............... | A61C 3/02 433/166 |
| 2010/0173263 A1 * | 7/2010 | Tetsuka | ............... | A61C 3/02 433/165 |
| 2010/0196844 A1 * | 8/2010 | Heo | ............... | A61C 3/02 433/114 |
| 2010/0266984 A1 * | 10/2010 | Jung | ............... | A61B 17/1688 433/166 |
| 2011/0195377 A1 * | 8/2011 | Sun | ............... | A61C 3/02 433/165 |
| 2011/0197517 A1 * | 8/2011 | Cantoni | ............... | A61C 3/02 51/309 |
| 2014/0106297 A1 * | 4/2014 | Schmidlin | ............... | A61C 3/00 433/82 |
| 2015/0097305 A1 * | 4/2015 | Hufschmied | ............... | A61C 3/02 264/16 |
| 2015/0147715 A1 * | 5/2015 | Breysse | ............... | A61B 17/1673 433/75 |
| 2015/0282895 A1 * | 10/2015 | Theorin | ............... | A61B 17/1615 433/165 |
| 2015/0298291 A1 * | 10/2015 | Wiand | ............... | B24D 3/06 51/307 |
| 2017/0245958 A1 * | 8/2017 | Smail | ............... | A61C 3/02 |
| 2018/0168772 A1 * | 6/2018 | Abboud | ............... | A61C 3/02 |
| 2018/0228577 A1 * | 8/2018 | Zacharia | ............... | A61C 1/084 |
| 2018/0235737 A1 * | 8/2018 | Chung | ............... | A61B 17/1673 |
| 2019/0125488 A1 * | 5/2019 | Ganss | ............... | A61C 5/42 |
| 2019/0343599 A1 * | 11/2019 | Brites | ............... | A61C 8/0089 |
| 2019/0365502 A1 * | 12/2019 | Goh | ............... | A61C 3/02 |
| 2020/0000550 A1 * | 1/2020 | Israel | ............... | A61C 1/084 |

FOREIGN PATENT DOCUMENTS

| | | |
|---|---|---|
| KR | 20-0352825 Y1 | 6/2004 |
| KR | 10-2010-0022024 A | 2/2010 |
| KR | 10-1344570 B1 | 12/2013 |

* cited by examiner

DRILLING DRIVER FOR PLACING DENTAL IMPLANT

CROSS-REFERENCE TO RELATED PATENT APPLICATION(S)

This application is the U.S. National Stage Entry of the International Application No. PCT/KR2016/008357, filed on Jul. 29, 2016, claiming priority to Korean Patent Application No. 10-2015-0122804, filed Aug. 31, 2015, the entire content of which is incorporated herein by reference in its entirety.

TECHNICAL FIELD

The present invention relates to a drilling driver for placing a dental implant.

BACKGROUND ART

Generally, in the absence of a tooth, an implant is fixed to the bone inside the gum and an artificial tooth is implanted thereon in many cases.

Here, according to environments in which the original tooth is located and a state thereof (e.g., a state of the bone in the corresponding portion, a relationship thereof with other teeth, a placement direction of the original tooth, a size of the original tooth, and the like), a shape of an implant to be implanted in the corresponding portion must be varied.

Among them, the most basic part of the implant placement is to drill the alveolar bone in accordance with an arrangement direction of the original tooth and with a depth corresponding to a tooth size.

However, in actually drilling the alveolar bone, it is not easy for a practitioner (or an operator) to check a state of the portion to be drilled. This is because, with a narrow working environment in the mouth, the practitioner's view is limited by a drilling driver itself.

Therefore, the practitioner may have difficulty in determining that there will be no problem in a direction or depth of drilling during a procedure and anticipating whether the implant will be eventually properly placed.

Technical Problem

An aspect of the present invention provides a drilling driver for placing a dental implant, capable of minimizing a visual field limitation by the drilling driver during a drilling procedure.

Technical Solution

According to an aspect of the present invention, there is provided a drilling driver for placing a dental implant including: a tip portion having a first outer diameter and having a cutting edge; a small-diameter portion extending from the tip portion and having a second outer diameter smaller than the first outer diameter; and a large-diameter portion located farther than the small-diameter portion with respect to the tip portion and having a third outer diameter larger than the first outer diameter.

Here, a difference between the first outer diameter and the second outer diameter may be smaller than a difference between the third outer diameter and the first outer diameter.

Here, the first outer diameter, the second outer diameter, and the third outer diameter may satisfy Equation 1 below:
[Equation 1] $1.8 < (D_3 - D_1)/(D_1 - D_2) < 2.3$, where $D_1$ is the first outer diameter, $D_2$ is the second outer diameter, and $D_3$ is the third outer diameter, all in units of mm.

Here, the difference between the first outer diameter and the second outer diameter may be half of the difference between the third outer diameter and the first outer diameter.

Here, the drilling driver may further include: a diameter expanding portion disposed between the small-diameter portion and the large-diameter portion and having an outer diameter gradually increased from the second outer diameter to the third diameter.

Here, the diameter expanding portion and the large-diameter portion account for 65% to 75% of the overall length of the driver.

Here, the drilling driver may further include: an induction portion provided in the small-diameter portion and inducing the small-diameter portion to be broken when an excessive force is applied to the driver.

Here, the induction portion may include an induction groove.

Here, the induction portion may include an induction groove extending in a circumferential direction of the small-diameter portion.

Here, the induction groove may be formed in an oblique direction with respect to the extending direction of the small-diameter portion.

Here, the induction portion may be positioned to be biased toward the large-diameter portion than the tip portion.

Advantageous Effects

According to the drilling driver for placing a dental implant according to the present invention configured as described above, it is possible to minimize a visual field limitation by the drilling driver during the drilling procedure.

BEST MODES

Figure 1:
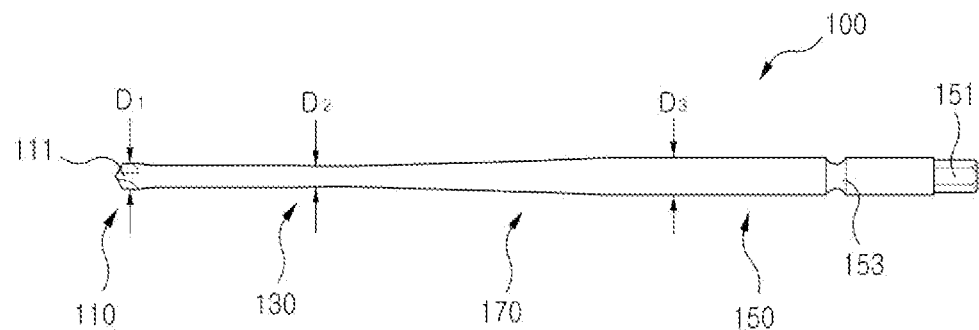
FIG. 1 is a side view of a drilling driver 100 for dental implant placement according to an embodiment of the present invention.

Hereinafter, a drilling driver for placing a dental implant according to a preferred embodiment of the present invention will be described in detail with reference to the accompanying drawings. In this disclosure, the same/similar reference numerals are given to the same/similar components although embodiments are different, and a description thereof will be replaced with a first description.

FIG. 1 is a side view of a drilling driver 100 for dental implant placement according to an embodiment of the present invention.

Referring to FIG. 1, the drilling driver 100 for dental implant placement may have a tip portion 110, a small-diameter portion 130, a large-diameter portion 150, and a diameter expanding portion 170.

The tip portion 110 is a portion including one end of the drilling driver 100. A cutting edge 111 is formed in the tip portion 110. The cutting edge 111 forms a recess in the alveolar bone when the drilling driver 100 rotates. The tip portion 110 has a first outer diameter $D_1$.

The small-diameter portion 130 is a portion extending from the tip portion 110. An outer diameter of the small-diameter portion 130 is a second outer diameter $D_2$, which is smaller than the first outer diameter $D_1$.

A large-diameter portion 150 is disposed next to the small-diameter portion 130 with respect to the tip portion 110. An outer diameter of the large-diameter portion 150 is a third outer diameter $D_3$, which is larger than the outer diameter $D_1$ of the tip portion 110. An insertion portion 151 and an engagement portion 153 may be formed on a free end side of the large-diameter portion 150. The insertion portion 151 is a portion to be inserted into a handpiece as an object in which the drilling driver 100 is installed and the engagement portion 153 is a portion to be caught by the handpiece.

The diameter expanding portion 170 is disposed between the small-diameter portion 130 and the large-diameter portion 150 to connect them. To this end, the diameter expanding portion 170 may have an outer diameter that gradually increases from the outer diameter $D_1$ of the small-diameter portion 130 to the outer diameter $D_3$ of the large-diameter portion 150.

Here, a difference between the first outer diameter $D_1$ and the second outer diameter $D_2$ may be smaller than a difference between the third outer diameter $D_3$ and the first outer diameter $D_1$.

Specifically, the first outer diameter $D_1$, the second outer diameter $D_2$, and the third outer diameter $D_3$ may satisfy Equation 1 below.

$$1.8 < (D_3 - D_1)/(D_1 - D_2) < 2.3 \quad \text{[Equation 1]}$$

{$D_1$ is the first outer diameter, $D_2$ is the second outer diameter, and $D_3$ is the third outer diameter, all in units of mm}

Here, if $(D_3 - D_1)/(D_1 - D_2)$ is 1.8 or less, the small-diameter portion 130 may be thicker than a set reference, making it difficult for a practitioner to visually check the recess formed by the cutting edge 111. Also, if $(D_3 - D_1)/(D_1 - D_2)$ is 2.3 or greater, strength of the small-diameter portion 130 may be excessively low, relative to the large-diameter portion 150. Therefore, the inventor of the present application confirmed that it is appropriate for the first outer diameter $D_1$ to the third outer diameter $D_3$ to satisfy the foregoing [Equation 1].

Specifically, the inventor set the first outer diameter $D_1$ to 2.2 mm, the second outer diameter $D_2$ to 1.8 mm, and the third outer diameter $D_3$ to 3.0 mm. Accordingly, $(D_3 - D_1)/(D_1 - D_2) = 3.0 - 2.2/2.2 - 1.8 = 0.8/0.4 = 2$.

The diameter expanding portion 170 and the large-diameter portion 150 may account for 65% to 75% of the entire length of the drilling driver 100. If the lengths of the diameter expanding portion 170 and the large-diameter portion 150 are less than 65% of the entire length of the drilling driver 100, a length of the small-diameter portion 130 may be increased to weaken overall strength of the drilling driver 100. If the lengths of the diameter expanding portion 170 and the large-diameter portion 150 are more than 75%, a vision of the practitioner may be covered by the diameter expanding portion 170 and the large-diameter portion 150, causing a problem.

According to such a configuration, the practitioner may relatively easily check the process of forming a recess through a space around the small-diameter portion 130, while the cutting edge 111 forms the recess in the alveolar bone. This is more reliably achieved by the relationship of $(D_3 - D_1)/(D_1 - D_2)$ according to the above-described [Equation 1], the ratio of the large-diameter portion 150 and the diameter expanding portion 170 in the overall length, and the like.

Hereinafter, a configuration for inducing fracture at the small-diameter portion 130 which is thinner than other portions will be described with reference to FIGS. 2 and 3.

Figure 2:
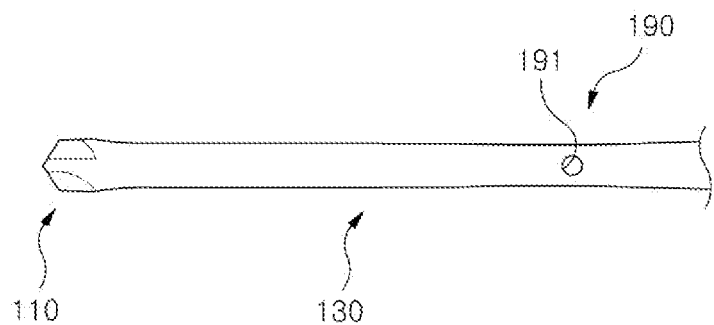
FIG. 2 is an enlarged partial side view of a small-diameter portion 130 of FIG. 1.

FIG. 2 is an enlarged partial side view of the small-diameter portion 130 of FIG. 1.

Referring to FIG. 2, an induction portion 190 may be provided in the small-diameter portion 130. The induction portion 190 is configured to induce a set portion of the small-diameter portion 130 to be broken when an excessive force is applied to the drilling driver 100.

As the induction portion 190, an induction groove 191 is exemplified in the present embodiment. The induction groove 191 may be a hole punched toward the center from an outer circumferential surface of the small-diameter portion 130. In addition, the induction groove 191 may be formed to penetrate through the small-diameter portion 130. Here, the induction groove 191 may be formed to be biased toward the diameter expanding portion 170, rather than to the tip portion 110.

Due to the configuration of the induction groove 191, the portion where the induction groove 191 is located may be broken when the relatively weak small-diameter portion 130 is broken. As a result, since the portion where the cutting edge 111 and the small-diameter portion 130 meet is broken, a problem in which a small piece of debris (almost of the tip portion 110 only) is stuck in the alveolar bone and is difficult to remove may be prevented.

Another configuration of the induction portion 190 will be described with reference to FIG. 3.

Figure 3:
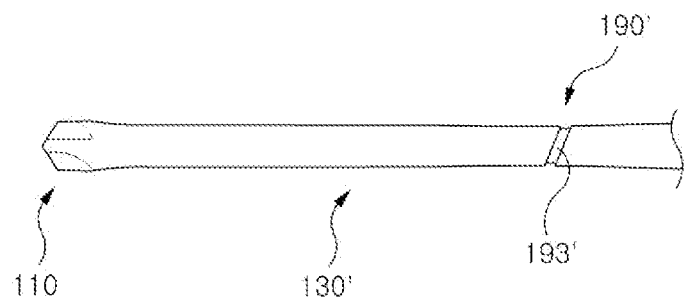
FIG. 3 is a partial side view illustrating a small-diameter portion 130' according to a modification of the small-diameter portion 130 of FIG. 2.

FIG. 3 is a partial side view illustrating a small-diameter portion 130' according to a modification of the small-diameter portion 130 of FIG. 2.

Referring to FIG. 3, the induction portion 190' may be an induction groove 193'. The induction groove 193' extends in a circumferential direction of a small-diameter portion 130'.

The induction groove 193' may be formed in an oblique direction with respect to the extending direction of the small-diameter portion 130'.

According to such a configuration, a portion where the induction groove 193' is formed may be broken by the induction groove 193' when the drilling driver receives an excessive force. Further, since the induction groove 193' is formed in the oblique direction, induction of fracture may be effectively made with respect to a twisting moment of the drilling driver.

The drilling driver for placing a dental implant as described above is not limited to the configuration and operation of the embodiments described above. The above embodiments may be configured so that all or some of the embodiments may be selectively combined to make various modifications.

INDUSTRIAL APPLICABILITY

The present invention is industrially applicable to the field of manufacturing a drilling driver for placing a dental implant.

What is claimed is:
1. A drilling driver for placing a dental implant, the drilling driver comprising:
a tip portion having a first outer diameter and having a cutting edge;

a small-diameter portion extending from the tip portion and having a second outer diameter smaller than the first outer diameter;

a large-diameter portion located farther than the small-diameter portion with respect to the tip portion and having a third outer diameter larger than the first outer diameter, a diameter expanding portion disposed between the small-diameter portion and the large-diameter portion and having an outer diameter gradually increased from the second outer diameter to the third diameter; and an induction portion provided in the small-diameter portion and configured to induce the small-diameter portion to be broken when excessive force is applied to the drilling driver, wherein the first outer diameter, the second outer diameter, and the third outer diameter satisfy the following relation:

$1.8 < (D_3 - D_1)/(D_1 - D_2) < 2.3$, where $D_1$ is the first outer diameter, $D_2$ is the second outer diameter, and $D_3$ is the third outer diameter, all in units of mm, and wherein the induction portion includes an induction groove formed in a position of the small-diameter portion or an induction groove extending in a circumferential direction of the small-diameter portion.

2. The drilling driver of claim 1, wherein a difference between the first outer diameter and the second outer diameter is smaller than a difference between the third outer diameter and the first outer diameter.

3. The drilling driver of claim 2, wherein the difference between the first outer diameter and the second outer diameter is half of the difference between the third outer diameter and the first outer diameter.

4. The drilling driver of claim 1, wherein the diameter expanding portion and the large-diameter portion account for 65% to 75% of an overall length of the driver.

5. The drilling driver of claim 1, wherein the induction groove is formed in an oblique direction with respect to an extending direction of the small-diameter portion.

6. The drilling driver of claim 1, wherein the induction portion is positioned to be biased toward the large-diameter portion than the tip portion.

* * * * *